(12) United States Patent
Tseng et al.

(10) Patent No.: US 11,590,265 B2
(45) Date of Patent: Feb. 28, 2023

(54) APPARATUSES AND METHODS FOR TREATING OPHTHALMIC DISEASES AND DISORDERS

(71) Applicant: TissueTech, Inc., Miami, FL (US)

(72) Inventors: Scheffer Tseng, Pinecrest, FL (US); Ek Kia Tan, Miami, FL (US)

(73) Assignee: BIOTISSUE HOLDINGS INC., Miami, FL (US)

(*) Notice: Subject to any disclaimer, the term of this patent is extended or adjusted under 35 U.S.C. 154(b) by 267 days.

(21) Appl. No.: 16/591,219

(22) Filed: Oct. 2, 2019

(65) Prior Publication Data

US 2020/0061250 A1    Feb. 27, 2020

Related U.S. Application Data (63) Continuation of application No. 15/051,477, filed on Feb. 23, 2016, now abandoned.

(60) Provisional application No. 62/119,544, filed on Feb. 23, 2015.

(51) Int. Cl.
| | |
|---|---|
| *A61L 31/00* | (2006.01) |
| *A61L 31/14* | (2006.01) |
| *A61L 31/16* | (2006.01) |
| *A61F 9/00* | (2006.01) |
| *A61N 1/04* | (2006.01) |
| *A61N 1/36* | (2006.01) |

(52) U.S. Cl.
CPC .......... *A61L 31/005* (2013.01); *A61F 9/0017* (2013.01); *A61L 31/146* (2013.01); *A61L 31/16* (2013.01); *A61L 2300/406* (2013.01); *A61L 2430/16* (2013.01); *A61N 1/0452* (2013.01); *A61N 1/36003* (2013.01)

(58) Field of Classification Search
CPC ............... A61F 9/0017; A61F 9/00772; A61F 9/00781; A61K 9/0051; A61K 9/0048
USPC ............................... 604/890.1, 891.1, 891.2
See application file for complete search history.

(56) References Cited

U.S. PATENT DOCUMENTS

| | | |
|---|---|---|
| 636,019 A | 10/1899 | Weyand |
| 3,598,122 A | 8/1971 | Zaffaroni et al. |
| 3,598,123 A | 8/1971 | Zaffaroni et al. |
| 3,710,795 A | 1/1973 | Higuchi et al. |
| 3,731,683 A | 5/1973 | Zaffaroni et al. |

(Continued)

FOREIGN PATENT DOCUMENTS

| | | |
|---|---|---|
| CN | 1871019 A | 11/2006 |
| CN | 1903073 A | 1/2007 |

(Continued)

OTHER PUBLICATIONS

Ahmed et al. Expression and localization of alphavbeta6 integrin in extraplacental fetal membranes: possible role in human parturition. Mol Hum Reprod 10(3):173-179 (2004).

(Continued)

*Primary Examiner* — Manuel A Mendez
(74) *Attorney, Agent, or Firm* — Wilson Sonsini Goodrich & Rosati (57) ABSTRACT

The invention relates generally to the fields of biology and health sciences. More particularly, the invention relates to compositions and methods for modulating cellular physiology and pathological processing using a combination of compounds that can be found in amniotic membrane tissue and umbilical cord tissue preparations.

16 Claims, 5 Drawing Sheets

(56) References Cited

U.S. PATENT DOCUMENTS

| | | | |
|---|---|---|---|
| 3,742,951 A | 7/1973 | Zaffaroni et al. | |
| 3,814,097 A | 6/1974 | Ganderton et al. | |
| 3,921,636 A | 11/1975 | Zaffaroni et al. | |
| 3,949,750 A * | 4/1976 | Freeman | A61F 9/00772 |
| | | | 606/107 |
| 3,972,995 A | 8/1976 | Tsuk et al. | |
| 3,993,072 A | 11/1976 | Zaffaroni et al. | |
| 3,993,073 A | 11/1976 | Zaffaroni et al. | |
| 3,995,635 A * | 12/1976 | Higuchi | A61F 9/0017 |
| | | | 604/294 |
| 3,996,934 A | 12/1976 | Zaffaroni et al. | |
| 4,031,894 A | 6/1977 | Urquhart et al. | |
| 4,060,084 A | 11/1977 | Chandrasekaran et al. | |
| 4,069,307 A | 1/1978 | Higuchi et al. | |
| 4,077,407 A | 3/1978 | Theeuwes et al. | |
| 4,100,022 A | 7/1978 | Ogasa et al. | |
| 4,120,649 A | 10/1978 | Schechter | |
| 4,184,360 A | 1/1980 | Vadnay et al. | |
| 4,201,210 A | 5/1980 | Hughes et al. | |
| 4,201,211 A | 5/1980 | Chandrasekaran et al. | |
| 4,230,105 A | 10/1980 | Harwood et al. | |
| 4,292,299 A | 9/1981 | Suzuki et al. | |
| 4,292,303 A | 9/1981 | Keith et al. | |
| 4,305,502 A | 12/1981 | Gregory et al. | |
| 4,327,725 A | 5/1982 | Cortese et al. | |
| 4,347,841 A | 9/1982 | Benyo et al. | |
| 4,361,552 A | 11/1982 | Baur, Jr. | |
| 4,476,116 A | 10/1984 | Anik | |
| 4,599,084 A | 7/1986 | Nashef | |
| 4,599,226 A | 7/1986 | Fox, Jr. et al. | |
| 4,624,848 A | 11/1986 | Lee | |
| 4,686,190 A | 8/1987 | Cramer et al. | |
| 4,787,885 A * | 11/1988 | Binder | A61F 9/00781 |
| | | | 604/294 |
| 4,798,611 A | 1/1989 | Freeman, Jr. | |
| 4,829,000 A | 5/1989 | Kleinman et al. | |
| 4,871,549 A | 10/1989 | Ueda et al. | |
| 4,915,684 A * | 4/1990 | MacKeen | A61F 9/00772 |
| | | | 604/294 |
| 4,968,509 A | 11/1990 | Radebaugh et al. | |
| 4,997,425 A | 3/1991 | Shioya et al. | |
| 5,002,071 A | 3/1991 | Harrell | |
| 5,011,692 A | 4/1991 | Fujioka et al. | |
| 5,017,381 A | 5/1991 | Maruyama et al. | |
| 5,075,104 A | 12/1991 | Gressel et al. | |
| 5,093,487 A | 3/1992 | Brown et al. | |
| 5,116,817 A | 5/1992 | Anik | |
| 5,135,915 A | 8/1992 | Czarniecki et al. | |
| 5,192,744 A | 3/1993 | Bouck et al. | |
| 5,229,135 A | 7/1993 | Philippon et al. | |
| 5,260,068 A | 11/1993 | Chen | |
| 5,260,069 A | 11/1993 | Chen | |
| 5,294,446 A | 3/1994 | Schlameus et al. | |
| 5,318,513 A | 6/1994 | Leib et al. | |
| 5,336,168 A | 8/1994 | Sibalis | |
| 5,352,668 A | 10/1994 | Burgeson et al. | |
| 5,437,287 A | 8/1995 | Phillips et al. | |
| 5,456,923 A | 10/1995 | Nakamichi et al. | |
| 5,461,140 A | 10/1995 | Heller et al. | |
| 5,472,436 A * | 12/1995 | Fremstad | A61K 9/0051 |
| | | | 623/905 |
| 5,474,490 A | 12/1995 | Allport | |
| 5,508,040 A | 4/1996 | Chen | |
| 5,516,527 A | 5/1996 | Curatolo | |
| 5,554,593 A | 9/1996 | Nakaya et al. | |
| 5,567,441 A | 10/1996 | Chen | |
| 5,622,721 A | 4/1997 | Dansereau et al. | |
| 5,665,378 A | 9/1997 | Davis et al. | |
| 5,665,596 A | 9/1997 | Mussi | |
| 5,686,105 A | 11/1997 | Kelm et al. | |
| 5,700,410 A | 12/1997 | Nakamichi et al. | |
| 5,728,396 A * | 3/1998 | Peery | A61K 9/0024 |
| | | | 424/424 |
| 5,837,280 A | 11/1998 | Kenealy et al. | |
| 5,837,284 A | 11/1998 | Mehta et al. | |
| 5,840,329 A | 11/1998 | Bai | |
| 5,869,090 A | 2/1999 | Rosenbaum | |
| 5,932,205 A | 8/1999 | Wang et al. | |
| 5,932,545 A | 8/1999 | Henkin et al. | |
| 5,977,175 A | 11/1999 | Lin | |
| 6,046,160 A | 4/2000 | Obi-Tabot | |
| 6,096,733 A | 8/2000 | Lubkin | |
| 6,143,315 A | 11/2000 | Wang et al. | |
| 6,152,142 A | 11/2000 | Tseng | |
| 6,162,193 A | 12/2000 | Ekberg | |
| 6,203,755 B1 | 3/2001 | Odland | |
| 6,254,637 B1 | 7/2001 | Lee et al. | |
| 6,326,019 B1 | 12/2001 | Tseng | |
| 6,391,452 B1 | 5/2002 | Antonsen et al. | |
| 6,465,014 B1 | 10/2002 | Moroni et al. | |
| 6,521,179 B1 | 2/2003 | Girardot et al. | |
| 6,573,249 B2 | 6/2003 | Lezdey et al. | |
| 6,632,648 B1 | 10/2003 | Kampinga et al. | |
| 6,923,983 B2 | 8/2005 | Morgan et al. | |
| 6,929,801 B2 | 8/2005 | Klose et al. | |
| 6,932,983 B1 | 8/2005 | Straub et al. | |
| 6,946,144 B1 | 9/2005 | Jordan | |
| 7,494,802 B2 | 2/2009 | Tseng et al. | |
| 8,071,135 B2 | 12/2011 | Liu et al. | |
| 8,105,634 B2 | 1/2012 | Liu et al. | |
| 8,153,162 B2 * | 4/2012 | Tseng | A61K 9/08 |
| | | | 424/583 |
| 8,182,840 B2 | 5/2012 | Tseng et al. | |
| 8,182,841 B2 | 5/2012 | Tseng et al. | |
| 8,187,639 B2 | 5/2012 | Tseng et al. | |
| 8,323,701 B2 | 12/2012 | Daniel et al. | |
| 8,372,437 B2 | 2/2013 | Daniel | |
| 8,420,126 B2 | 4/2013 | Tseng et al. | |
| 8,440,235 B2 | 5/2013 | Tseng et al. | |
| 8,455,009 B2 | 6/2013 | Tseng et al. | |
| 8,460,714 B2 | 6/2013 | Tseng et al. | |
| 8,840,665 B2 | 9/2014 | Young et al. | |
| 8,932,805 B1 | 1/2015 | Brahm | |
| 8,961,617 B2 | 2/2015 | Young | |
| 8,980,630 B2 | 3/2015 | Woodbury et al. | |
| 9,132,156 B1 * | 9/2015 | Werber | A61K 8/982 |
| 9,161,954 B2 | 10/2015 | Tseng et al. | |
| 9,161,955 B2 | 10/2015 | Tseng et al. | |
| 9,161,956 B2 | 10/2015 | Tseng et al. | |
| 9,162,011 B2 | 10/2015 | Stilwell et al. | |
| 9,180,145 B2 | 11/2015 | Brown et al. | |
| 9,198,939 B2 | 12/2015 | Tseng et al. | |
| 9,205,150 B2 | 12/2015 | Jarrett et al. | |
| 9,498,327 B1 | 11/2016 | Brahm | |
| 9,662,355 B2 | 5/2017 | Koob et al. | |
| 9,682,044 B2 | 6/2017 | Tseng et al. | |
| 9,682,160 B2 | 6/2017 | Tseng et al. | |
| 9,694,109 B1 | 7/2017 | Brahm | |
| 9,724,370 B2 | 8/2017 | Tseng et al. | |
| 9,750,771 B2 | 9/2017 | Tseng et al. | |
| 9,750,772 B2 | 9/2017 | Tseng et al. | |
| 9,795,639 B1 | 10/2017 | Brahm | |
| 9,801,975 B2 | 10/2017 | Stilwell et al. | |
| 9,801,976 B2 | 10/2017 | Stilwell et al. | |
| 9,803,176 B2 | 10/2017 | Patel et al. | |
| 9,814,746 B2 | 11/2017 | Werber et al. | |
| 9,821,013 B2 | 11/2017 | Mcfetridge et al. | |
| 9,827,293 B2 | 11/2017 | Koob et al. | |
| 9,913,466 B2 | 3/2018 | Chang et al. | |
| 9,919,078 B1 | 3/2018 | Brahm | |
| 9,920,301 B2 | 3/2018 | Taghizadeh | |
| 9,931,423 B2 | 4/2018 | Tseng et al. | |
| 9,944,900 B2 | 4/2018 | Gage et al. | |
| 9,956,248 B2 | 5/2018 | Tom et al. | |
| 9,956,252 B2 | 5/2018 | Tseng et al. | |
| 9,993,506 B1 | 6/2018 | Brahm | |
| 10,006,003 B2 | 6/2018 | Spencer et al. | |
| 10,029,030 B2 | 7/2018 | Koob et al. | |
| 10,039,793 B2 | 8/2018 | Brown et al. | |
| 10,066,202 B2 | 9/2018 | Woodbury et al. | |
| 10,105,397 B2 | 10/2018 | Morse et al. | |
| 10,220,059 B2 | 3/2019 | Kihm et al. | |
| 10,258,456 B2 | 4/2019 | Morita et al. | |

(56) References Cited

U.S. PATENT DOCUMENTS

| | | | |
|---|---|---|---|
| 10,272,119 B2 | 4/2019 | Tseng et al. | |
| 10,314,688 B2 | 6/2019 | Shepard et al. | |
| 10,568,914 B1 | 2/2020 | Brahm | |
| 10,688,220 B2 | 6/2020 | Hopkinson et al. | |
| 2003/0064093 A1 | 4/2003 | Jordan | |
| 2003/0143280 A1* | 7/2003 | El-Sherif | A61K 31/717 424/490 |
| 2003/0180181 A1 | 9/2003 | Greib et al. | |
| 2003/0187515 A1 | 10/2003 | Hariri et al. | |
| 2004/0043026 A1 | 3/2004 | Tuan et al. | |
| 2004/0057938 A1 | 3/2004 | Ghinelli | |
| 2004/0059430 A1 | 3/2004 | Kim et al. | |
| 2004/0126323 A1 | 7/2004 | Shevchuk et al. | |
| 2004/0126878 A1 | 7/2004 | Ramos et al. | |
| 2004/0209235 A1 | 10/2004 | Goldstein et al. | |
| 2005/0064391 A1 | 3/2005 | Segal et al. | |
| 2006/0078993 A1 | 4/2006 | Phan et al. | |
| 2007/0048292 A1 | 3/2007 | Morita et al. | |
| 2007/0299386 A1 | 12/2007 | Peyman | |
| 2008/0050814 A1 | 2/2008 | Allickson | |
| 2008/0102135 A1 | 5/2008 | Ollivier | |
| 2008/0131522 A1 | 6/2008 | Liu et al. | |
| 2008/0193554 A1 | 8/2008 | Dua et al. | |
| 2008/0286378 A1 | 11/2008 | Behrens et al. | |
| 2010/0272782 A1 | 10/2010 | Owens et al. | |
| 2011/0208300 A1 | 8/2011 | De, Jr. et al. | |
| 2011/0212158 A1 | 9/2011 | Tom et al. | |
| 2011/0307059 A1 | 12/2011 | Young et al. | |
| 2011/0311491 A1 | 12/2011 | Edinger et al. | |
| 2012/0003296 A1 | 1/2012 | Shantha et al. | |
| 2012/0010708 A1 | 1/2012 | Young et al. | |
| 2012/0010727 A1 | 1/2012 | Young et al. | |
| 2012/0020933 A1 | 1/2012 | Young et al. | |
| 2012/0035743 A1 | 2/2012 | Young et al. | |
| 2012/0035744 A1 | 2/2012 | Young et al. | |
| 2012/0136322 A1 | 5/2012 | Alster et al. | |
| 2012/0141595 A1 | 6/2012 | Tseng et al. | |
| 2012/0263731 A1 | 10/2012 | Fraunhofer et al. | |
| 2012/0294909 A1 | 11/2012 | Daniel et al. | |
| 2012/0294910 A1 | 11/2012 | Daniel et al. | |
| 2013/0144128 A1 | 6/2013 | De, Jr. et al. | |
| 2013/0156863 A1 | 6/2013 | Tseng et al. | |
| 2013/0172829 A1* | 7/2013 | Badawi | A61F 9/0017 604/294 |
| 2013/0197665 A1 | 8/2013 | Daniel et al. | |
| 2013/0209524 A1 | 8/2013 | Young | |
| 2013/0211502 A1 | 8/2013 | Young | |
| 2013/0211504 A1 | 8/2013 | Young | |
| 2013/0211511 A1 | 8/2013 | Young | |
| 2013/0236506 A1 | 9/2013 | Young | |
| 2013/0238100 A1 | 9/2013 | Young | |
| 2013/0289724 A1 | 10/2013 | Young | |
| 2013/0344162 A1 | 12/2013 | Morse et al. | |
| 2013/0344163 A1 | 12/2013 | Tseng et al. | |
| 2014/0050788 A1 | 2/2014 | Daniel et al. | |
| 2014/0052247 A1 | 2/2014 | Daniel et al. | |
| 2014/0052274 A1 | 2/2014 | Koob et al. | |
| 2014/0106447 A1 | 4/2014 | Brown et al. | |
| 2014/0121612 A1 | 5/2014 | Rubin et al. | |
| 2014/0205646 A1 | 7/2014 | Morse et al. | |
| 2014/0255496 A1 | 9/2014 | Daniel et al. | |
| 2014/0271776 A1 | 9/2014 | Vines et al. | |
| 2014/0294780 A1 | 10/2014 | Mcfetridge et al. | |
| 2014/0302162 A1 | 10/2014 | Morse et al. | |
| 2015/0017255 A1 | 1/2015 | Koob et al. | |
| 2015/0086634 A1 | 3/2015 | Koob et al. | |
| 2015/0110850 A1 | 4/2015 | Daniel | |
| 2015/0182661 A1 | 7/2015 | Daniel | |
| 2015/0190279 A1 | 7/2015 | Acharya et al. | |
| 2015/0216912 A1 | 8/2015 | Koob | |
| 2015/0250829 A1 | 9/2015 | Daniel et al. | |
| 2015/0320906 A1 | 11/2015 | Broussard et al. | |
| 2015/0328264 A1 | 11/2015 | Lucey et al. | |
| 2015/0335686 A1 | 11/2015 | Spencer et al. | |
| 2016/0022695 A1* | 1/2016 | Reich | A61P 27/08 514/613 |
| 2016/0066566 A1 | 3/2016 | Chang et al. | |
| 2016/0067287 A1 | 3/2016 | Mcqueen et al. | |
| 2016/0082152 A1 | 3/2016 | Brahm | |
| 2016/0106785 A1 | 4/2016 | Tseng et al. | |
| 2016/0131924 A1 | 5/2016 | Thompson | |
| 2016/0184368 A1 | 6/2016 | Tseng et al. | |
| 2016/0243288 A1 | 8/2016 | Tseng et al. | |
| 2016/0303171 A1 | 10/2016 | Tseng et al. | |
| 2016/0324902 A1 | 11/2016 | Tseng et al. | |
| 2016/0346332 A1 | 12/2016 | Spencer et al. | |
| 2017/0027993 A1 | 2/2017 | Ichim | |
| 2017/0136071 A1 | 5/2017 | Danilkovitch et al. | |
| 2017/0203004 A1 | 7/2017 | Murphy et al. | |
| 2017/0252380 A1 | 9/2017 | Cox, Jr. et al. | |
| 2017/0260500 A1 | 9/2017 | Goodman et al. | |
| 2017/0368105 A1 | 12/2017 | Sinclair et al. | |
| 2018/0008649 A1 | 1/2018 | Aberman et al. | |
| 2018/0017577 A1 | 1/2018 | Franco | |
| 2018/0055622 A1 | 3/2018 | Tokish et al. | |
| 2018/0059109 A1 | 3/2018 | Hsuan et al. | |
| 2018/0110900 A1 | 4/2018 | Korenfeld | |
| 2018/0112184 A1 | 4/2018 | Kim et al. | |
| 2018/0117121 A1 | 5/2018 | Koob et al. | |
| 2018/0119093 A1 | 5/2018 | Kukharchuk et al. | |
| 2018/0126036 A1 | 5/2018 | Early | |
| 2018/0127721 A1 | 5/2018 | Phan | |
| 2018/0132908 A1 | 5/2018 | Brahm et al. | |
| 2018/0133261 A1 | 5/2018 | Herzberg et al. | |
| 2018/0140641 A1 | 5/2018 | Harrell | |
| 2018/0163177 A1 | 6/2018 | Lo et al. | |
| 2018/0177716 A1 | 6/2018 | Noh et al. | |
| 2018/0177989 A1 | 6/2018 | Prentice | |
| 2018/0193387 A1 | 7/2018 | Tseng et al. | |
| 2018/0221418 A1 | 8/2018 | Daniel et al. | |
| 2018/0264049 A1 | 9/2018 | Wagner et al. | |
| 2018/0271914 A1 | 9/2018 | Steed et al. | |
| 2018/0271917 A1 | 9/2018 | Fu | |
| 2018/0338998 A1 | 11/2018 | Petrucci | |
| 2018/0338999 A1 | 11/2018 | Brown et al. | |
| 2018/0344777 A1 | 12/2018 | Harris et al. | |
| 2018/0344900 A9 | 12/2018 | Brown et al. | |
| 2018/0346874 A1 | 12/2018 | Harris et al. | |
| 2018/0362920 A1 | 12/2018 | Guo | |
| 2018/0362923 A1 | 12/2018 | Guo | |
| 2018/0362932 A1 | 12/2018 | Guo | |
| 2019/0040355 A1 | 2/2019 | Woodbury et al. | |
| 2019/0070335 A1 | 3/2019 | Karagianis | |
| 2019/0105351 A9 | 4/2019 | Kramer et al. | |
| 2019/0105352 A9 | 4/2019 | Brown et al. | |
| 2019/0127702 A1 | 5/2019 | Kerkis et al. | |
| 2019/0134100 A1 | 5/2019 | Cao et al. | |
| 2019/0134265 A1 | 5/2019 | Semler et al. | |
| 2019/0141987 A1 | 5/2019 | Patel et al. | |
| 2019/0177684 A1 | 6/2019 | Ha et al. | |
| 2020/0077987 A1 | 3/2020 | Harrell | |

FOREIGN PATENT DOCUMENTS

| | | |
|---|---|---|
| CN | 1972678 A | 5/2007 |
| EP | 0669138 A2 | 8/1995 |
| EP | 1604695 A1 | 12/2005 |
| JP | 74043153 B | 11/1974 |
| JP | H01256967 A | 10/1989 |
| KR | 20010098716 A | 11/2001 |
| WO | WO-9837903 A1 | 9/1998 |
| WO | WO-03077794 A2 | 9/2003 |
| WO | WO-03097809 A2 | 11/2003 |
| WO | WO-2004026244 A2 | 4/2004 |
| WO | WO-2004060388 A1 | 7/2004 |
| WO | WO-2005060988 A1 | 7/2005 |
| WO | WO-2006094247 A2 | 9/2006 |
| WO | WO-2007038686 A2 | 4/2007 |
| WO | WO-2007071048 A1 | 6/2007 |
| WO | WO-2011031489 A2 | 3/2011 |
| WO | WO-2012003377 A2 | 1/2012 |

(56) References Cited

FOREIGN PATENT DOCUMENTS

| WO | WO-2012170905 A1 | 12/2012 |
|---|---|---|
| WO | WO-2014066775 A1 | 5/2014 |
| WO | WO-2016138025 A2 | 9/2016 |

OTHER PUBLICATIONS

Allred et al. A novel ELISA for measuring CD36 protein in human adipose tissue. J Lipid Res 2(2):408-415 (2011).
Azuara-Blanco et al. Amniotic Membrane Transplantation for Ocular Surface Reconstruction. Br. J. Ophthalmol. 83(4):399-402 (1999).
Azuara-Blanco et al. Amniotic Membrane Transplantation for Ocular Surface Reconstruction. Invest. Ophthalmol. Vis. Sci. 39(4):S428 (1998).
Badawy et al. Evaluation of Tissue Healing and Adhesion Formation After an Intraabdominal Amniotic Membrane Graft in the Rat. J. Reproductive Med. 34:198 (1989).
Bae et al. Characterization of the Promoter Region of the Human Transforming Growth Factor-β Type II Receptor Gene. J. Biol. Chem. 270(49):29460-29468 (1995).
Barton et al. Amniotic membrane transplantation in glaucoma surgery. Invest Ophthalmol Vis Sci 38:S473 (1997).
Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).
Border et al. Transforming Growth Factor-β in Disease: The Dark Side of Tissue Repair. J. Clin. Invest. 90:1-7 (1992).
Budenz et al. Amniotic Membrane Transplantation for Repair of Leaking Glaucoma Filtering Blebs. Am. J. Ophthalmol. 130:580-588 (2000).
Chen et al. Amniotic Membrane Transplantation for Severe Neurotrophic Corneal Ulcers. Br. J. Ophthalmol. 84:826-833 (2000).
Chen et al. Functions of hyaluronan in wound repair. Wound Rep Reg 7:79-89 (1999).
Chen et al. Recombinant Adenovirus Coexpressing Covalent Peptide/MHC Class II Complex and B7-1: In Vitro and In Vivo Activation of Myelin Basic Protein-Specific T Cells. J. Immunol. 167:1297-1305 (2001).
Cho et al. Conjunctival Epithelial Cells Cultured on Human Amniotic Membrane Do Not Transdifferentiate into Corneal Epithelial Type Cells. Invest. Ophthalmol. Vis. Sci. 39(4):S428 (1998).
Cho et al. Conjunctival Epithelial Cells Cultured on Human Amniotic Membrane Fail To Transdifferentiate into Corneal Epithelial-type Cells. Cornea 18:216-224 (1999).
Choi et al. Effect of the Application of Human Amniotic Membrane on Rabbit Corneal wound Healing After Excimer Laser Photorefractive Keratectomy. Cornea 17:389-395 (1998).
Day et al. Hyaluronan cross-linking: a protective mechanism in inflammation? Trends in Immunology 26(12):637-643 (2005).
Derotth. Plastic Repair of Conjunctival Defects with Fetal Membranes. Archives of Ophthalmology 23:522-525 (1940).
Derynk et al. TGF-β receptor signaling. Biochem. Biophys. Acta. 1333:F105-F150 (1997).
Dua et al. Amniotic Membrane Transplantation. Br. J. Ophthalmol. 83:748-752 (1999).
English Translation of JP74043153B (App. S45-107284) (9 pgs.) (Pub. Nov. 19, 1974).
Ericsson et al. Chapter 17: Protein extraction from solid tissue. Methods Mol Biol. 675:307-312 (2011).
Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).
Fortunato et al. Interleukin-10 inhibition of interleukin-6 in human amniochorionic membrane: Transcriptional regulation. Am. J. Obstet. Gynecol. 175:1057-1065 (1996).
Fortunato et al. The effect of transforming growth factor and interleukin-10 on interleukin-8 release by human amniochorion may regulate histologic chorioamnionitis. Am. J. Obstet. Gynecol. 179(3):794-799 (1998).
Franch et al. Human Amniotic Membrane Transplantation. Invest. Ophthalmol. Vis. Sci. 39(4):S90 (1998).
Fries et al. Inter-alpha-inhibitor, hyaluronan and inflammation. Acta Biochim Polonica 50(3):735-742 (2003).
Fujishima et al. Trabeculectomy With the Use of Amniotic Membrane for Uncontrolled Glaucoma, Ophthalmic. Surg. Lasers 29:428-431 (1998).
Fukuda et al. Differential Distribution of Subchains of the Basement Membrane Components Type IV Collagen and Laminin Among the Amniotic Membrane, Cornea, and Conjunctiva. Cornea 18:73-79 (1999).
Gabbiani. The myofibroblast in wound healing and fibrocontractive diseases. J. Pathol. 200:500-503 (2003).
Gajiwala et al. Evaluation of lyophilised, gamma-irradiated amnion as a biological dressing. Cell Tissue Bank 5(2):73-80 (2004).
Grande. Role of Transforming Growth Factor-β in Tissue Injury and Repair. Proc. Soc. Exp. Biol. Med. 214:27-40 (1997).
Guo. Carbopol® Polymers for Pharmaceutical Drug Delivery Applications. Drug Delivery Technology 3(6):1-4 (2003).
Hales et al. TGF-β-1 induces lens cells to accumulate α-smooth muscle actin, a marker for subcapsular cataracts. Curr. Eye Res. 13:885-890 (1994).
Hall et al. Liquid Extraction Surface Analysis Mass Spectrometry Method for Identifying the Presence and Severity of Nonalcoholic Fatty Liver Disease. Anal. Chem. 89(9):5161-5170 (2017).
Hanada et al. Regulation of cytokine signaling and inflammation. Cytokine & Growth Factor Reviews 13(4-5):413-421 (2002).
Hao et al. Identification of Antiangiogenic and Antiinflammatory Proteins in Human Amniotic Membrane. Cornea 19(3):348-352 (2000).
Hatano et al. Transplantation of amniotic membrane and limbal autograft in the treatment of recurrent pterygium. Clinical Ophthalmology 50(6):1101-1104 (1996) (English Abstract).
He et al. A simplified system for generating recombinant adenoviruses. PNAS USA 95:2509-2514 (1998).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).
He et al. Suppression of activation and induction of apoptosis in RAW264.7 cells by amniotic membrane extract. Invest Ophthalmol. Vis. Sci. 49:4468-4475 (2008).
Hilmy et al. Physical and chemical properties of freeze-dried amnio-chorion membranes sterilized by y irradiation. Atom Indonesia 13(2):1-3 (1987) Abstract only.
Hori. Amniotic Membrane Transplantation and Immune Reaction. Folia Ophthalmologica Japonica 56(9):722-727 (2005) (English Abstract).
Howes et al. Receptor for Advanced Glycation End Products and Age-Related Macular Degeneration. Invest. Ophthalmol. Vis. Sci. 45(10):3713-3720 (2004).
Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 21:38-43 (2000).
Kim et al. Amniotic Membrane Patching Promotes Healing and Inhibits Protease Activity on Wound Healing Following Acute Corneal Alkali Burns. Exp. Eye Res. 70:329-337 (1998).
Kim et al. Clinical Uses of Human Amniotic Membrane for Ocular Surface Diseases. In: Advances in Corneal Research, Lass, J.H. ed. (NY: Plenum Press), pp. 117-134 (1997).

(56) References Cited

OTHER PUBLICATIONS

Kim et al. Temporary Amniotic Membrane Graft Promotes Healing and Inhibits Protease Activity in Corneal Wound Induced by Alkali Burn in Rabbits. Invest. Ophthalmol. Vis. Sci. 39(4):S90 (1998).
Kim et al. The Effects on Inhibition of Corneal Neovascularization After Human Amniotic Membrane Transplantation in Severely Damaged Rabbit Corneas. Korean J. Ophthalmol. 9:32-46 (1995).
Kim et al. Transplantation of Preserved Human Amniotic Membrane for Surface Reconstruction in Severely Damaged Rabbit Corneas. Cornea 15:473-84 (1995).
Klen. Influence of Ionizing Sterilization on the Permeability of Human Chorio-Amniotic, Dermo-Epidermal and Fascial Grafts. Res. Exp. Med. 167(1):15-21 (1976).
Koizumi et al. Amniotic Membrane as a Substrate for Cultivating Limbal Corneal Epithelial Cells for Autologous Transplantation in Rabbits. Cornea 19:65-71 (2000).
Koizumi et al. Cultivation of Corneal Epithelial Cells on Intact and Denuded Human Amniotic Membrane. Invest. Ophthalmol. Vis. Sci. 41:2506-2513 (2000).
Koizumi et al. Growth Factor mRNA and Protein in Preserved Human Amniotic Membrane. Curr. Eye Res. 20:173-177 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kruse et al. Cryopreserved Human Amniotic Membrane For Ocular Surface Reconstruction. Graefe's Arch. Clin. Exp. Ophthalmol. 238:68-75 (2000).
Kruse et al. Multilayer Amniotic Membrane Transplantation for Reconstruction of Deep Corneal Ulcers. Ophthalmology 106:1504-1511 (1999).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Kuznetsova et al. The N-terminal module of thrombospondin-1 interacts with the link domain of TSG-6 and enhances its covalent association with the heavy chains of inter-alpha-trypsin inhibitor. J Biol Chem 280:30899-30908 (2005).
Lawrence. Transforming Growth Factor-β: a general review. Eur. Cytokine Netw. 7:363-374 (1996).
Lee et al. An Agarose Gel Electrophoretic Method for Analysis of Hyaluronan Molecular Weight Distribution. Anal. Biochem. 219:278-287 (1994).
Lee et al. Suppression of TGF-β signaling in both normal conjunctival fibroblasts and pterygial body fibroblasts by amniotic membrane. Curr. Eye Res. 20(4):325-334 (2000).
Li et al. An Experimental Study of the Effects of Human Amniotic Membrane on Human Retinal Pigment Epithelial Cell Proliferation in vitro. Acta Acadamiae Medicinae Militaris Tertia 25(5):407-409 (2003) (English Abstract).
Li et al. Reversal of myofibroblasts by amniotic membrane stromal extract. J Cell Physiol. 215(3):657-664 (2008).
Lieberman et al. Pharmaceutical Dosage Forms. 2 Ed. 1:209-214 (1990).
Liu et al. E-cadherin engagement stimulates proliferation via Rac1. Journal of Cell Biology 173(3):431-441 (2006).
Logan et al. Decorin Attenuates Gliotic Scar Formation in the Rat Cerebral Hemisphere. Exp. Neurol. 159:504-510 (1999).
Ma et al. Amniotic Membrane Graft for Primary Pterygium: Comparison with Conjunctival Autograft and Topical Mitomycin C Treatment. Br. J. Ophthalmol. 84:973-978 (2000).
Marek et al. TGF-β-(transforming growth factor-β) in chronic inflammatory conditions—a new diagnostic and prognostic marker? Med. Sci. Monitl. 8(7):RA145-RA151 (2002).
Massague et al. Controlling TGF-β signaling. Genes and Development 14:627-644 (2000).
Meller et al. Amniotic Membrane Transplantation for Acute Chemical or Thermal Burns. Ophthalmology. 107:980-990 (2000).
Meller et al. Amniotic Membrane Transplantation for Symptomatic Conjunctivochalasis Refractory to Medical Treatments. Cornea 19:796-803 (2000).
Meller et al. Conjunctival Epithelial Cell Differentiation on Amniotic Membrane. Invest. Ophthalmol. Vis. Sci. 40:878-886 (1999).
Meller et al. In Vitro Conjunctival Epithelial Differentiation on Preserved Human Amniotic Membrane. Invest. Ophthalmol. Vis. Sci. 39(4):S428 (1998).
Moller-Pedersen et al. Neutralizing antibody to TGF-β modulates stromal fibrosis but not regression of photoablative effect following PRK. Curr. Eye Res. 17:736-747 (1998).
Monteleone et al. SMAD7 in TGF-β-mediated negative regulation of gut inflammation. Trends in Immunology 25(10):513-517 (2004).
Na et al. Analysis of Human Amniotic Membrane Components as Proteinase Inhibitors for Development of Therapeutic Agent for Recalcitrant Keratitis. Trophoblast Res. 13:453-466 (1999).
Na et al. Analysis of Human Amniotic Membrane Components as Proteinase Inhibitors for Development of Therapeutic Agent of Recalcitrant Keratitis. Invest. Ophthalmol. Vis. Sci. 39(4):S90 (1998).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Nguyen et al. Sterilization of allograft bone: effects of gamma irradiations on allograft biology and biomechanics. Cell Tissue Banking 8:93-105 (2007).
Ochsner et al. Decreased expression of tumor necrosis factor-alpha-stimulated gene 6 in cumulus cells of the cyclooxygenase2 and EP2 null mice. Endocrinology 144:1008-1019 (2003).
Oikawa et al. Inhibition of Angiogenesis by 15-Deoxyspergualin. J. Antibiotics 44(9):1033-1035 (1991).
Park et al. Modulation of Acute Inflammation and Keratocyte Death by Suturing, Blood and Amniotic Membrane in PRK. Invest. Ophthalmol. Vis. Sci. 41:2906-2914 (2000).
Park et al. Temperature Cooling Reduces Keratocyte Death in Excimer Laser Ablated Corneal and Skin Wounds. Invest. Ophthalmol. Vis. Sci. 39(4):S449 (1998).
PCT/US1998/03665 International Search Report dated Jun. 23, 1998.
PCT/US2003/07853 International Search Report dated Feb. 26, 2004.
PCT/US2006/37906 International Preliminary Report on Patentability dated Apr. 1, 2008.
PCT/US2006/37906 International Search Report and Written Opinion dated Jul. 11, 2007.
PCT/US2010/46675 International Preliminary Report on Patentability dated Feb. 28, 2012.
PCT/US2010/46675 International Search Report and Written Opinion dated May 30, 2011.
PCT/US2011/042679 International Preliminary Report on Patentability dated Jan. 8, 2013.
PCT/US2011/042679 International Search Report and Written Opinion dated Mar. 9, 2012.
PCT/US2012/052358 International Preliminary Report on Patentability dated Mar. 4, 2014.
PCT/US2012/052358 International Search Report and Written Opinion dated Jan. 31, 2013.
PCT/US2016/019174 International Preliminary Report on Patentability dated Sep. 8, 2017.
PCT/US2016/019174 International Search Report and Written Opinion dated Aug. 12, 2016.
PCT/US2017/015325 Invitation to Pay Additional Fees dated Apr. 10, 2017.

(56) References Cited

OTHER PUBLICATIONS

Petraglia et al. Inhibin and Activin in Human Fetal Membranes: Evidence of a Local Effect on Prostaglandin Release. J. Clin. Endocrinol. Metab. 77(2):542-548 (1993).
Pires et al. Amniotic Membrane Transplantation for Symptomatic Bullous Keratopathy. Arch. Ophthalmol. 117(10):1291-1297 (1999).
Pires et al. Amniotic Membrane Transplantation or Limbal Conjunctival Autograft for Limbal Stem Cell Deficiency Induced by 5-fluorouracil in Glaucoma Surgeries. Cornea 19:284-287 (2000).
Prabhasawat et al. Impression Cytology Study of Epithelial Phenotype of Ocular Surfaces Reconstructed by Preserved Human Amniotic Membrane. Arch Ophthalmol. 115:1360-1367 (Nov. 1997).
Relucenti et al. Cumulus oophorus extracellular matrix in the human oocyte: a role for adhesive proteins. Ital J Anat Embryol 110(2 Supp 1):219-224 (2005).
Riau et al. Preservation, sterilization and de-epithelialization of human amniotic membrane for use in ocular surface reconstruction. Biomaterials 31:216-225 (2010).
Riley et al. Production of inhibin forms by the fetal membranes, decidua, placenta and fetus at parturition. Hum. Reprod. 15:578-583 (2000).
Rodriguez-Ares et al. Repair of Scleral Perforation with Preserved Scleral and Amniotic Membrane in Marfan's Syndrome. Ophthalmic Surg. Lasers 30(6):485-487 (1999).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Saltzman. Drug Administration and Drug Effectiveness. Chapter 2. Drug Delivery-Engineering Principles for Drug Therapy. Oxford Press. p. 9-19 (2001).
Salustri et al. PTX3 plays a key role in the organization of the cumulus oophorus extracellular matrix and in in vivo fertilization. Development 131:1577-1586 (2004).
Sato et al. Role of Growth Factors for Ocular Surface Reconstruction After Amniotic Membrane Transplantation. Invest. Ophthalmol. Vis. Sci. 39(4):S428 (1998).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Shimazaki et al. Amniotic Membrane Transplantation for Ocular Surface Reconstruction in Patients with Chemical and Thermal Burns. Ophthalmology. 104(12):2068-2076 (1997).
Shimazaki et al. Transplantation of Amniotic Membrane and Limbal Autograft for Patients with Recurrent Pterygium Associated with Symblepharon. Br. J. Ophthalmol. 82(3):235-240 (1998).
Shortt et al. The effect of amniotic membrane preparation method on its ability to serve as a substrate for the ex-vivo expansion of limbal epithelial cells. Biomaterials 30:1056-1065 (2009).
Singh et al. Dried gamma-irradiation amniotic membrane as dressing in burn wound care. Journal of Tissue Viability 20:49-54 (2011).
Singh et al. Microbiological safety and clinical efficacy of radiation sterilized amniotic membranes for treatment of second-degree burns. Burns 33:505-510 (2007).
Solomon et al. Suppression of Interleukin 1a and interleukin 1b in human limbal epithelial cells cultured on the amniotic membrane stromal matrix. Br. J. Ophthalmol 85:444-449 (2001).
Sorsby et al. Amniotic Membrane Grafts in Caustic Burns of the Eye (Burns of the Second Degree). Br. J. Ophthalmology 30:337-345 (1946).
Sorsby et al. Further Experience with Amniotic Membrane Grafts in Caustic Burns of the Eye. Br. J. Ophthalmology 31:409-418 (1947).
Sorsby. Amniotic Membrane Grafts in Burns. In: Modern Trends in Ophthalmology. Sorsby, A. ed. (NY: Paul B. Hoeber, Inc.), pp. 504-510 (1947).
Sur et al. Anti-inflammatory and anti-platelet aggregation activity of human placental extract. Acta Pharmacol Sin 24(2):187-192 (2003).
Tan et al. Structural and Biological Comparison of Cryopreserved and Fresh Amniotic membrane Tissues. Journal Biomaterial and Tissue Engineering 4:379-388 (2014).
Taylor et al. Rate of Re-epithelialization Following Amniotic Membrane Transplantation. Invest. Ophthalmol. Vis. Sci. 39(4):S1038 (1998).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Trelford. The Amnion in Surgery, Past and Present. Am J. Obstet. Gynecol 134:833 (1979).
Tsai et al. Reconstruction of Damaged Corneas by Transplantation of Autologous Limbal Epithelial cells. New Eng. J. Med. 343(2): 86-93 (2000).
Tsai. Corneal Surfaces Reconstruction by Amniotic Membrane with Cultivated Autologous Limbo-Corneal Epithelium. Invest. Ophthalmol. Vis. Sci. 39(4):S429 (1998).
Tseng et al. Amniotic Membrane Transplantation for Conjunctival Surface Reconstruction. Am. J. Ophthalmol. 124:765-774 (Dec. 1997).
Tseng et al. Down-regulation of TGF-β1, β2, β3 and TGF-β Receptor II Expression in Human Corneal Fibroblasts by Amniotic Membrane. Invest. Ophthalmol. Vis. Sci. 39(4):S428 (1998).
Tseng et al. How Does Amniotic Membrane Work? Ocular Surface J. 2(3):177-187 (2004).
Tseng et al. Suppression of Transforming Growth Factor-Beta Isoforms, TGF-β Receptor Type II, and Myofibroblast Differentiation in Cultured Human Corneal and Limbal Fibroblasts by Amniotic Membrane Matrix. J. Cell Physiol. 179:325-335 (1999).
Tsubota et al. Surgical Reconstruction of the Ocular Surface in Advanced Ocular Cicatricial Pemphigoid and Stevens-Johnson Syndrome. Am J Ophthalmology 122:38-52 (1996).
U.S. Appl. No. 09/027,109 Office Action dated Dec. 7, 1999.
U.S. Appl. No. 09/027,109 Office Action dated Jun. 5, 2000.
U.S. Appl. No. 10/472,117 Office Action dated Oct. 18, 2007.
U.S. Appl. No. 11/528,902 Office Action dated Apr. 2, 2009.
U.S. Appl. No. 11/528,902 Office Action dated Dec. 16, 2009.
U.S. Appl. No. 11/528,902 Office Action dated Jan. 27, 2011.
U.S. Appl. No. 11/528,902 Office Action dated Sep. 8, 2010.
U.S. Appl. No. 11/528,980 Office Action dated Aug. 11, 2009.
U.S. Appl. No. 11/528,980 Office Action dated Jan. 10, 2011.
U.S. Appl. No. 11/528,980 Office Action dated Nov. 13, 2008.
U.S. Appl. No. 11/528,980 Office Action dated Oct. 15, 2010.
U.S. Appl. No. 11/529,658 Office Action dated Apr. 3, 2009.
U.S. Appl. No. 11/529,658 Office Action dated Dec. 16, 2009.
U.S. Appl. No. 11/529,658 Office Action dated Jan. 27, 2011.
U.S. Appl. No. 11/529,658 Office Action dated Sep. 3, 2010.
U.S. Appl. No. 11/535,924 Office Action dated Dec. 16, 2009.
U.S. Appl. No. 11/535,924 Office Action dated Jan. 31, 2011.
U.S. Appl. No. 11/535,924 Office Action dated Mar. 31, 2009.
U.S. Appl. No. 11/535,924 Office Action dated Sep. 8, 2010.
U.S. Appl. No. 13/322,896 Office Action dated Jan. 20, 2016.
U.S. Appl. No. 13/322,896 Office Action dated Jul. 6, 2015.
U.S. Appl. No. 13/322,896 Office Action dated Oct. 22, 2014.
U.S. Appl. No. 13/322,896 Office Action dated Oct. 4, 2016.
U.S. Appl. No. 13/322,896 Office Action dated Sep. 6, 2017.
U.S. Appl. No. 13/453,840 Office Action dated Aug. 21, 2012.
U.S. Appl. No. 13/704,231 Office Action dated Aug. 16, 2017.
U.S. Appl. No. 13/704,231 Office Action dated Aug. 2, 2016.
U.S. Appl. No. 13/704,231 Office Action dated Feb. 11, 2016.
U.S. Appl. No. 13/704,231 Office Action dated Jan. 19, 2017.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.

(56) References Cited

OTHER PUBLICATIONS

U.S. Appl. No. 13/802,204 Office Action dated Jan. 22, 2016.
U.S. Appl. No. 13/802,204 Office Action dated Jun. 15, 2018.
U.S. Appl. No. 13/802,204 Office Action dated Oct. 4, 2016.
U.S. Appl. No. 13/802,204 Office Action dated Sep. 7, 2017.
U.S. Appl. No. 13/802,264 Office Action dated Jul. 16, 2015.
U.S. Appl. No. 13/802,264 Office Action dated Nov. 28, 2014.
U.S. Appl. No. 13/802,359 Office Action dated Dec. 10, 2014.
U.S. Appl. No. 13/802,447 Office Action dated Dec. 15, 2014.
U.S. Appl. No. 14/240,712 Office Action dated Apr. 6, 2017.
U.S. Appl. No. 14/240,712 Office Action dated Nov. 27, 2015.
U.S. Appl. No. 14/240,712 Office Action dated Nov. 28, 2016.
U.S. Appl. No. 14/729,489 Office Action dated Dec. 7, 2016.
U.S. Appl. No. 14/819,319 Office Action dated Apr. 1, 2016.
U.S. Appl. No. 14/819,319 Office Action dated Oct. 2, 2015.
U.S. Appl. No. 14/848,143 Office Action dated Jun. 21, 2017.
U.S. Appl. No. 14/848,143 Office Action dated Oct. 20, 2016.
U.S. Appl. No. 14/848,148 Office Action dated Mar. 20, 2017.
U.S. Appl. No. 14/848,148 Office Action dated Oct. 28, 2016.
U.S. Appl. No. 14/848,153 Office Action dated Apr. 21, 2017.
U.S. Appl. No. 14/848,153 Office Action dated Oct. 25, 2016.
U.S. Appl. No. 14/880,135 Office Action dated Dec. 23, 2016.
U.S. Appl. No. 14/886,946 Office Action dated Apr. 18, 2016.
U.S. Appl. No. 14/886,946 Office Action dated Jan. 8, 2018.
U.S. Appl. No. 14/886,946 Office Action dated May 19, 2017.
U.S. Appl. No. 14/886,946 Office Action dated May 28, 2019.
U.S. Appl. No. 14/886,946 Office Action dated Oct. 5, 2016.
U.S. Appl. No. 14/886,946 Office Action dated Sep. 7, 2018.
U.S. Appl. No. 14/996,051 Office Action dated Apr. 2, 2018.
U.S. Appl. No. 14/996,051 Office Action dated Jul. 24, 2017.
U.S. Appl. No. 14/996,051 Office Action dated May 28, 2019.
U.S. Appl. No. 14/996,051 Office Action dated Sep. 7, 2018.
U.S. Appl. No. 15/051,477 Office Action dated Apr. 9, 2019.
U.S. Appl. No. 15/195,189 Office Action dated May 30, 2018.
U.S. Appl. No. 15/215,228 Office Action dated May 30, 2018.
U.S. Appl. No. 15/636,227 Office Action dated Sep. 27, 2018.
U.S. Appl. No. 15/879,042 Office Action dated Jul. 8, 2019.
Verbeek et al. Induction of alpha-smooth muscle actin expression in cultured human brain pericytes by transforming growth factor-beta 1. Am. J. Pathol. 144:372-382 (1994).
Wang et al. Corneal Haze is Reduced by Amniotic Membrane Matrix in Excimer Laser Photoablation in Rabbits. Invest Ophthalmol Vis Sci 38:S405 (1997).
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).
Wu et al. Wound healing effects of porcine placental extracts on rats with thermal injury. Br J Dermatol 148(2):236-245 (2003).
Yamaguchi et al. Negative regulation of transforming growth factor-$\beta$ by the proteoglycan decorin. Nature 346(6281):281-284 (1990).
Yokomori et al. Advantages and Pitfalls of Amnion Inversion Repair for the Treatment of Large Unruptured Omphalocele: Results of 22 Cases. Journal of Pediatric Surgery 23:882-884 (1992).
Yoshida. Placenta Power: For Health and Beauty—A useful guide for those seeking placenta-based remedies. Downloaded from http://www.melsmon.co.jp/img/commom/PlacentaPowerp002-121_04-09-08.pdf. (p. 1-41) (Aug. 2001).
Yosuf et al. Challenges in validating the sterilisation dose for processed human amniotic membranes. Radiation Physics and Chemistry 76:1756-1756 (2007).
Sood et al. Gene expression patterns in human placenta. PNAS 103(16):5478-5483 (2006).
U.S. Appl. No. 14/996,051 Office Action dated Dec. 5, 2019.

\* cited by examiner

APPARATUSES AND METHODS FOR TREATING OPHTHALMIC DISEASES AND DISORDERS

CROSS-REFERENCE TO RELATED APPLICATIONS

This application is a continuation of U.S. application Ser. No. 15/051,477, filed on Feb. 23, 2016, which claims benefit of U.S. Provisional Application No. 62/119,544, filed Feb. 23, 2015, entitled "Apparatuses and Methods For Treating Ophthalmic Diseases and Disorders," the contents of each are incorporated herein by reference in their entireties.

FIELD OF THE INVENTION

The invention relates generally to the fields of biology and health sciences. More particularly, the invention relates to compositions and methods for modulating cellular physiology and pathological processing using a combination of compounds that can be found in amniotic membrane tissue and umbilical cord tissue preparations.

BACKGROUND

With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose.

Tears are produced by several glands in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes, symptoms of dry eye can develop.

Tears are made up of three layers: oil, water, and mucus. Each component serves a function in protecting and nourishing the front surface of the eye. A smooth oil layer helps to prevent evaporation of the water layer, while the mucin layer functions in spreading the tears evenly over the surface of the eye. If the tears evaporate too quickly or do not spread evenly over the cornea due to deficiencies with any of the three tear layers, dry eye symptoms can develop.

The most common form of dry eyes is due to an inadequate amount of the water layer of tears. This condition, called keratoconjunctivitis sicca (KCS), is also referred to as dry eye syndrome.

People with dry eyes may experience symptoms of irritated, gritty, scratchy, or burning eyes, a feeling of something in their eyes, excess watering, and blurred vision due to nerve loss or nerve damage in the cornea. Advanced dry eyes may damage the front surface of the eye and impair vision.

Traditionally ocular surface reconstruction has been used to treat acute chemical and thermal burns of the eye. This form of ocular surface reconstruction involves suturing a protective and/or therapeutic covering over the surface of the eye.

A variety of ophthalmic and non-ophthalmic conditions necessitate administration of various drugs to the eye. Eye drops and gels can be effective drug delivery vehicles, but can also have significant disadvantages. Specifically, eye drops mix with fluid in the tear film, but may have a residence time of only 2-5 minutes in the tear film. As little as 5% of the drug may be absorbed locally; some or all of the rest being carried from the lacrimal sac into the lacrimal duct, which can have potentially undesirable effects. Consequently, most of the drug may be wasted with less than ideal amounts delivered to the targeted tissue. Also, the presence of the drug in the bloodstream may have potentially harmful side effects. Gels may adhere more effectively to the eye, but can also blur the patient's vision. Both eye drops and gels may need to be reapplied frequently for some therapies, and patients may not administer the eye drops or gels as frequently as directed in at least some instances, such that the amount of drug delivered can be less than ideal. For example, in at least some instances a substantial number of patients may not refill their prescription after one year, and the substantial number of patients can be up to fifty percent in some instances.

Current treatments for dry eyes aim to restore or maintain the normal amount of tears in the eye to minimize dryness and related discomfort and to maintain eye health while current treatments for acute chemical and thermal burns require the use of sutures. What is needed is an apparatus that can be inserted into the eye of a patient that will induce blinking and may optionally deliver one or more therapeutic agents to the eye of the patient and further may optionally cover the surface of the eye with a therapeutic agent.

SUMMARY

In one embodiment the current application describes an apparatus for treating dry eye or other diseases or disorders of the eye, by insertion of the device onto the surface of the eye of a patient in need thereof, wherein the apparatus comprises: one or more flexible tubular structures, wherein the one or more flexible tubular structures comprise a material selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); polyurethane (PU); umbilical cord tissue; amniotic membrane tissue; placental tissue; chorion tissue and any combination thereof.

In one embodiment the current application describes an apparatus for treating dry eye or other diseases or disorders of the eye, by insertion of the apparatus onto the surface of the eye of a patient in need thereof, wherein the apparatus comprises: one or more flexible tubular structures, wherein the one or more flexible tubular structures comprise a material selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); polyurethane (PU); umbilical cord tissue; amniotic membrane tissue; placental tissue; chorion tissue and any combination thereof; and one or more flexible fastening cuffs, wherein the inner surface of the one or more flexible fastening cuffs are frictionally engaging the outer surface of the one or more flexible tubular structures.

In one embodiment the current application describes an apparatus for treating dry eye or other diseases or disorders of the eye, by insertion of the device onto the surface of the eye of a patient in need thereof, wherein the apparatus comprises: at least one sheet comprising a material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof; and at least one tubular structure comprising a second material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof, wherein at least one sheet and at least one tubular structure are adhering to maintain physical contact with one another.

In one embodiment the current application describes an apparatus for treating dry eye or other diseases or disorders of the eye, by insertion of the device onto the surface of the eye of a patient in need thereof, wherein the apparatus comprises: at least one first sheet comprising a material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof; and at least one second sheet comprising a second material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof, wherein the at least one first sheet and the at least one second sheet are adhering to maintain physical contact with one another.

In certain embodiments the current application describes the use of an apparatus according to the current application to promote an increase in tissue sensation, to induce a patient to blink and tear more frequently to prevent dry eye, to promote nerve growth, promote nerve regeneration or a combination thereof in a contacted tissue, to reduce an inflammatory response in a contacted tissue, to increase Tear Breakup Time in a patient suffering from dry eye disease, to increase tear osmolarity in a patient suffering from dry eye disease, to decrease corneal straining in a patient suffering from dry eye disease, to increase the score on Schirmer's test in a patient suffering from dry eye disease or combinations thereof.

DETAILED DESCRIPTION

A description of preferred embodiments of the current application follows. It will be understood that the particular embodiments of the application are shown by way of illustration and not as limitations of the application. At the outset, the embodiments are described in their broadest overall aspects, with a more detailed description following. The features and other details of the apparatuses and uses of the embodiments will be further pointed out in the claims.

The present application is directed to apparatuses and uses of the apparatuses for treating dry eye or other diseases or disorders of the eye.

Figure 1:
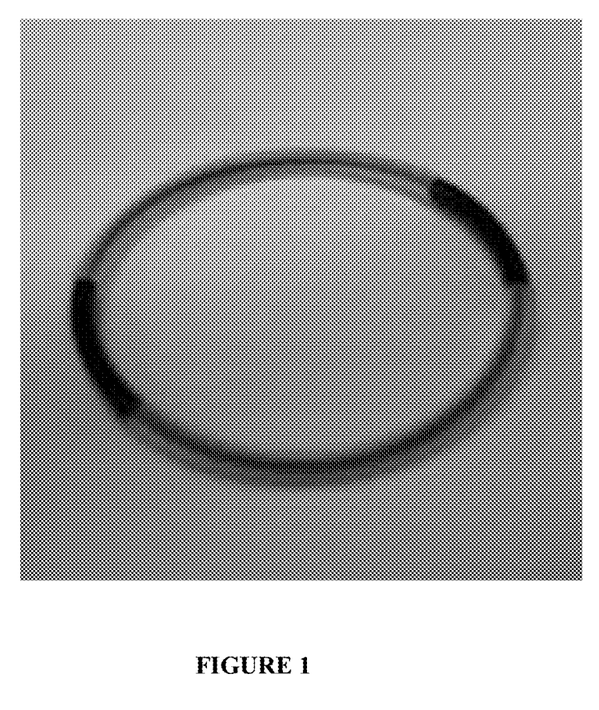
FIG. 1—Illustrates an apparatus of the present application, wherein the apparatus comprises: one or more flexible tubular structures having at least one porous inlet and at least one porous outlet.

In a first embodiment the current application describes an apparatus for treating dry eye or other diseases or disorders of the eye, by insertion of the device onto the surface of the eye of a patient in need thereof, wherein the apparatus comprises: one or more flexible tubular structures, wherein the one or more flexible tubular structures comprise a material selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); polyurethane (PU); umbilical cord tissue; amniotic membrane tissue; placental tissue; chorion tissue and any combination thereof. In some embodiments the apparatus is configured to reside in at least one of the group consisting of: superior conjunctiva fornix, inferior conjunctiva fornix and combinations thereof. While in other embodiments the apparatus is configured to reside in both conjunctiva fornices. In certain embodiments the apparatus deepen the fornix tear reservoir by stretching the conjunctival sac. In some embodiments the apparatus induces blinking.

In other embodiments the one or more flexible tubular structures have a length of about 0.5 cm to about 15 cm, a circumference of about 2 cm to about 15 cm or a circumference of about 4 cm to about 12 cm, an outside diameter of about 0.5 cm to about 5.0 cm or an outside diameter of about 1.2 cm to about 3.5 cm, a cross sectional diameter of about 0.01 cm to about 1.0 cm or a cross sectional diameter of about 0.05 cm to about 0.2 cm.

In certain embodiments the one or more flexible tubular structures the one or more flexible tubular structures contain at least one porous inlet and at least one porous outlet and the at least one porous inlet and the at least one porous outlet taken together form an osmotic pump when in contact with tears in the patient's eye.

Figure 4:
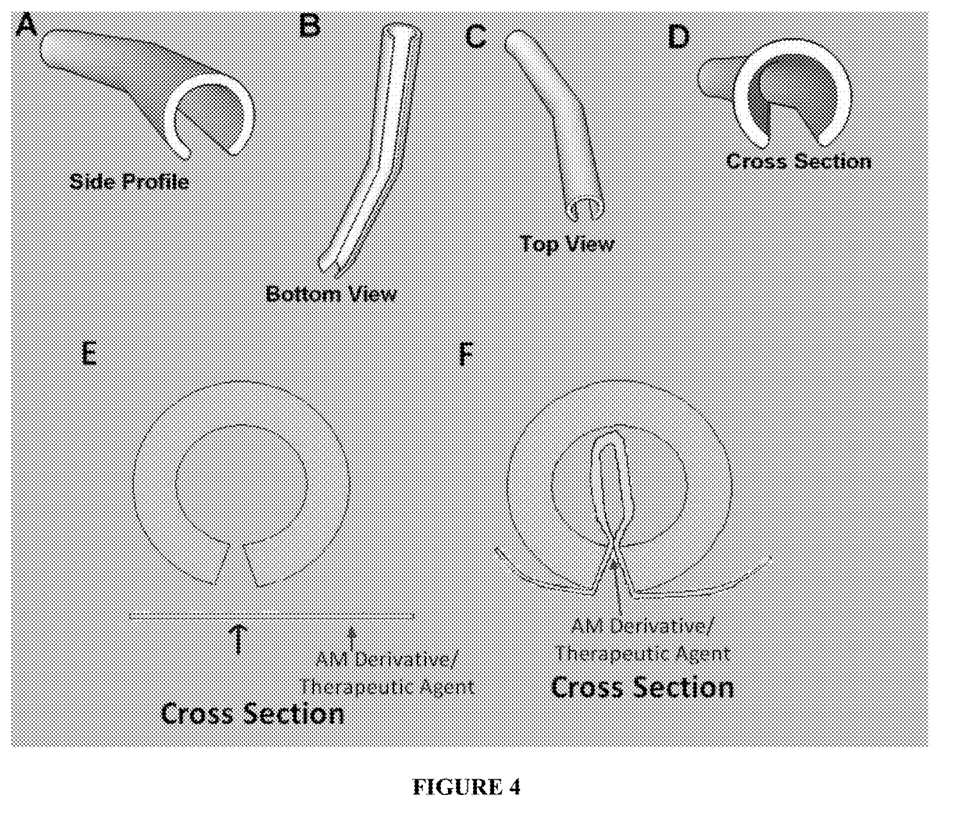
FIG. 4—Illustrates an apparatus of the present application, wherein the apparatus comprises: one or more flexible tubular structures having at least one porous inlet and at least one porous outlet, wherein the opening defined by the outer circumference of the one or more flexible tubular structures is covered by a sheet frictionally engaged on the flexible tubular structure.

In further embodiments the apparatus is configured to deliver one or more therapeutic agents to the patient, the therapeutic agent is delivered by diffusion through the net movement of solute from an area of high concentration to an area of low concentration, the therapeutic agent is delivered through compression of the apparatus via blinking, the one or more therapeutic agents may be incorporated into the material of the one or more flexible tubular structures, on the surface of the one or more flexible tubular structures, inside the one or more flexible tubular structures or combinations thereof, the one or more flexible tubular structures are configured to dissolve when in contact with tears in the patient's eye, the one or more therapeutic agents may be frictionally engaged onto a surface of the one or more flexible tubular structures, into the one or more flexible tubular structures or a combination thereof, the one or more therapeutic agents may be one or more sheets covering from about 25% to about 100% of the opening defined by the outer circumference of the one or more flexible tubular structures, the one or more therapeutic agents is selected from the group consisting of: antibacterial antibiotics, synthetic antibacterials, antifungal antibiotics, synthetic antifungals, umbilical cord tissue, amniotic membrane tissue, placental tissue, chorion tissue, antineoplastic agents, steroidal anti-inflammatory agents, non-steroidal anti-inflammatory agents, anti-allergic agents, glaucoma-treating agents, antiviral agents, and anti-mycotic agents, wherein the one of more therapeutic agents may be dispersed in a polymer, wherein the polymer is selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); and polyurethane (PU), wherein the umbilical cord tissue, amniotic membrane tissue, placental tissue or chorion tissue may be present in any form from the group consisting of: lyophilized, fresh, sheet, morselized, powder matrix, extract, purified extract, previously frozen, suspension and on a physiologically acceptable support.

In some embodiments the apparatus further comprises a power source at least one positive electrode and at least one negative electrode wherein the apparatus is configured to introduce an electrical stimulus between about 0.1 milliamps and about 50 milliamps to the muscles of the patient's eyelids.

Figure 2:
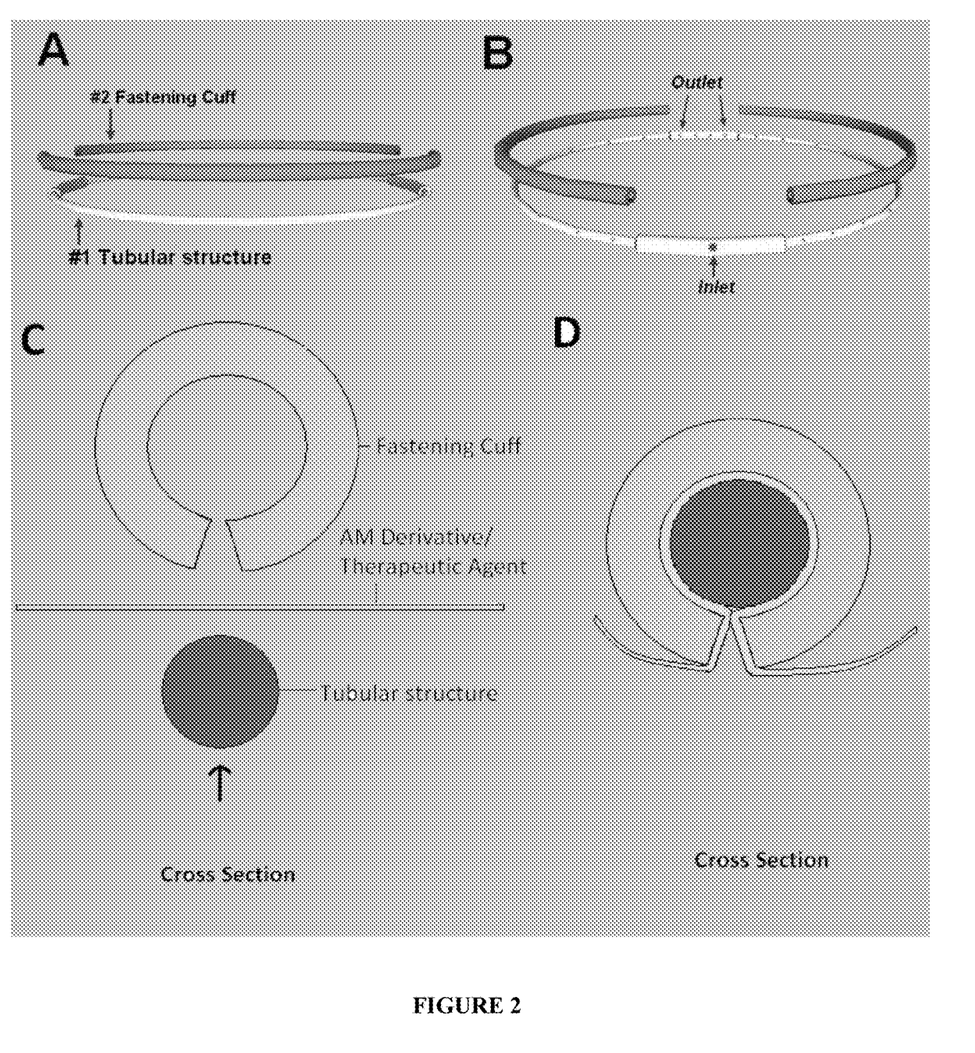
FIG. 2—Illustrates an apparatus of the present application, wherein the apparatus comprises: one or more flexible tubular structures having at least one porous inlet and at least one porous outlet; and one or more flexible fastening cuffs, wherein the inner surface of the one or more flexible fastening cuffs are frictionally engaging the outer surface of the one or more flexible tubular structures.

In a second embodiment the current application describes an apparatus for treating dry eye or other diseases or disorders of the eye, by insertion of the apparatus onto the surface of the eye of a patient in need thereof, wherein the apparatus comprises: one or more flexible tubular structures, wherein the one or more flexible tubular structures comprise a material selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); polyurethane (PU); umbilical cord tissue; amniotic membrane tissue; placental tissue; chorion tissue and any combination thereof; and one or more flexible fastening cuffs, wherein the inner surface of the one or more flexible fastening cuffs are frictionally engaging the outer surface of the one or more flexible tubular structures. In some embodiments the apparatus is configured to reside in at least one of the group consisting of: superior conjunctiva fornix, inferior conjunctiva fornix and combinations thereof. In other embodiments the apparatus is configured to reside in both conjunctiva fornices. In certain embodiments the apparatus deepen the fornix tear reservoir by stretching the conjunctival sac. In still other embodiments the apparatus induces blinking.

In some embodiments the one or more flexible tubular structures have a length of about 0.5 cm to about 15 cm, a circumference of about 2 cm to about 15 cm or a circumference of about 4 cm to about 12 cm, an outside diameter of about 0.5 cm to about 5.0 cm or an outside diameter of about 1.2 cm to about 3.5 cm, a cross sectional diameter of about 0.01 cm to about 1.0 cm or a cross sectional diameter of about 0.05 cm to about 0.2 cm.

In certain embodiments the one or more flexible tubular structures the one or more flexible tubular structures contains at least one porous inlet and at least one porous outlet and the at least one porous inlet and the at least one porous outlet taken together form an osmotic pump when in contact with tears in the patient's eye.

Figure 3:
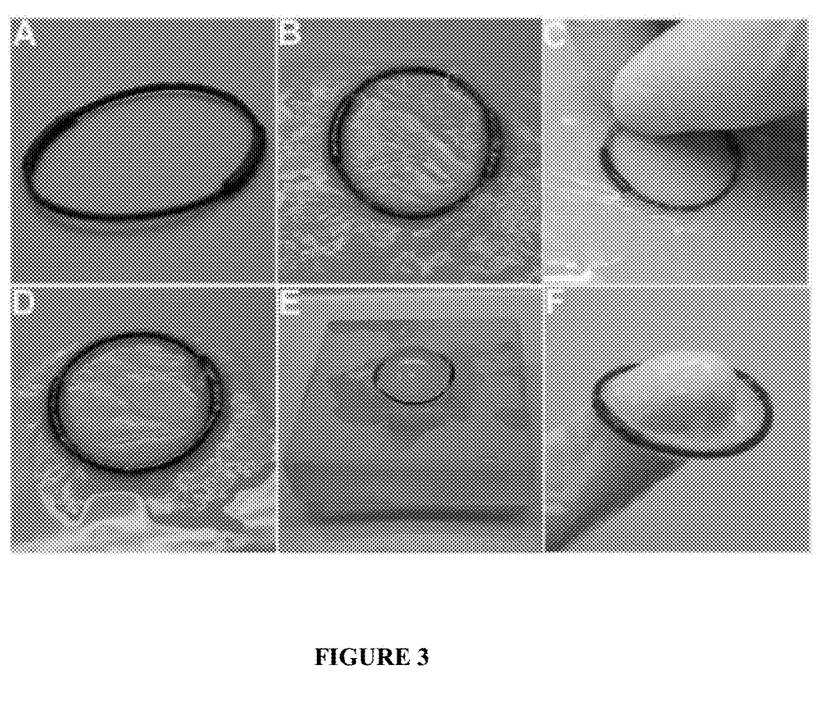
FIG. 3—Illustrates an apparatus of the present application, wherein the apparatus comprises: one or more flexible tubular structures having at least one porous inlet and at least one porous outlet; and one or more flexible fastening cuffs, wherein the opening defined by the outer circumference of the one or more flexible tubular structures is covered by a sheet frictionally engaged between the one or more flexible fastening cuffs and the flexible tubular structure.

In some embodiments the apparatus is configured to deliver one or more therapeutic agents to the patient, the therapeutic agent is delivered by diffusion through the net movement of solute from an area of high concentration to an area of low concentration, the therapeutic agent is delivered through compression of the apparatus via blinking, the one or more therapeutic agents may be delivered from the one or more flexible fastening cuffs, the one or more flexible tubular structures or a combination thereof, the one or more therapeutic agents may be incorporated into the material of the one or more flexible fastening cuffs, on the surface of the one or more flexible fastening cuffs or combinations thereof, the one or more flexible fastening cuffs are configured to dissolve when in contact with tears in the patient's eye, the one or more therapeutic agents may be incorporated into the material of the flexible tubular structure, on the surface of the flexible tubular structure, inside the flexible tubular structure or combinations thereof, the one or more flexible tubular structures are configured to dissolve when in contact with tears in the patient's eye, the one or more therapeutic agents may be frictionally engaged between the one or more flexible fastening cuffs and the flexible tubular structure, the one or more therapeutic agents may be one or more sheets covering from about 25% to about 100% of the opening defined by the outer circumference of the flexible tubular structure, the one or more therapeutic agents is selected from the group consisting of: antibacterial antibiotics, synthetic antibacterials, antifungal antibiotics, synthetic antifungals, umbilical cord tissue, amniotic membrane tissue, placental tissue, chorion tissue, antineoplastic agents, steroidal anti-inflammatory agents, non-steroidal anti-inflammatory agents, anti-allergic agents, glaucoma-treating agents, antiviral agents, and anti-mycotic agents, wherein the one of more therapeutic agents may be dispersed in a polymer, wherein the polymer is selected from the group consisting of: ethylene vinyl acetate (EVA); polydimethylsiloxane (PDMS); polymethylmetacrylate (PMMA); polyethylene teraphthalate (PET); polycarbonate (PC); hydrogels; polyvinyl chloride (PVC); rubber; latex; polyethylene (PE); silicone; polytetrafluoroethylene (PTFE); and polyurethane (PU), wherein the umbilical cord tissue, amniotic membrane tissue, placental tissue or chorion tissue may be present in any form from the group consisting of: lyophilized, fresh, sheet, morselized, powder matrix, extract, purified extract, previously frozen, suspension and on a physiologically acceptable support.

In other embodiments the apparatus further comprises a power source at least one positive electrode and at least one negative electrode wherein the apparatus is configured to introduce an electrical stimulus between about 0.1 milliamps and about 50 milliamps to the muscles of the patient's eyelids.

Figure 5:
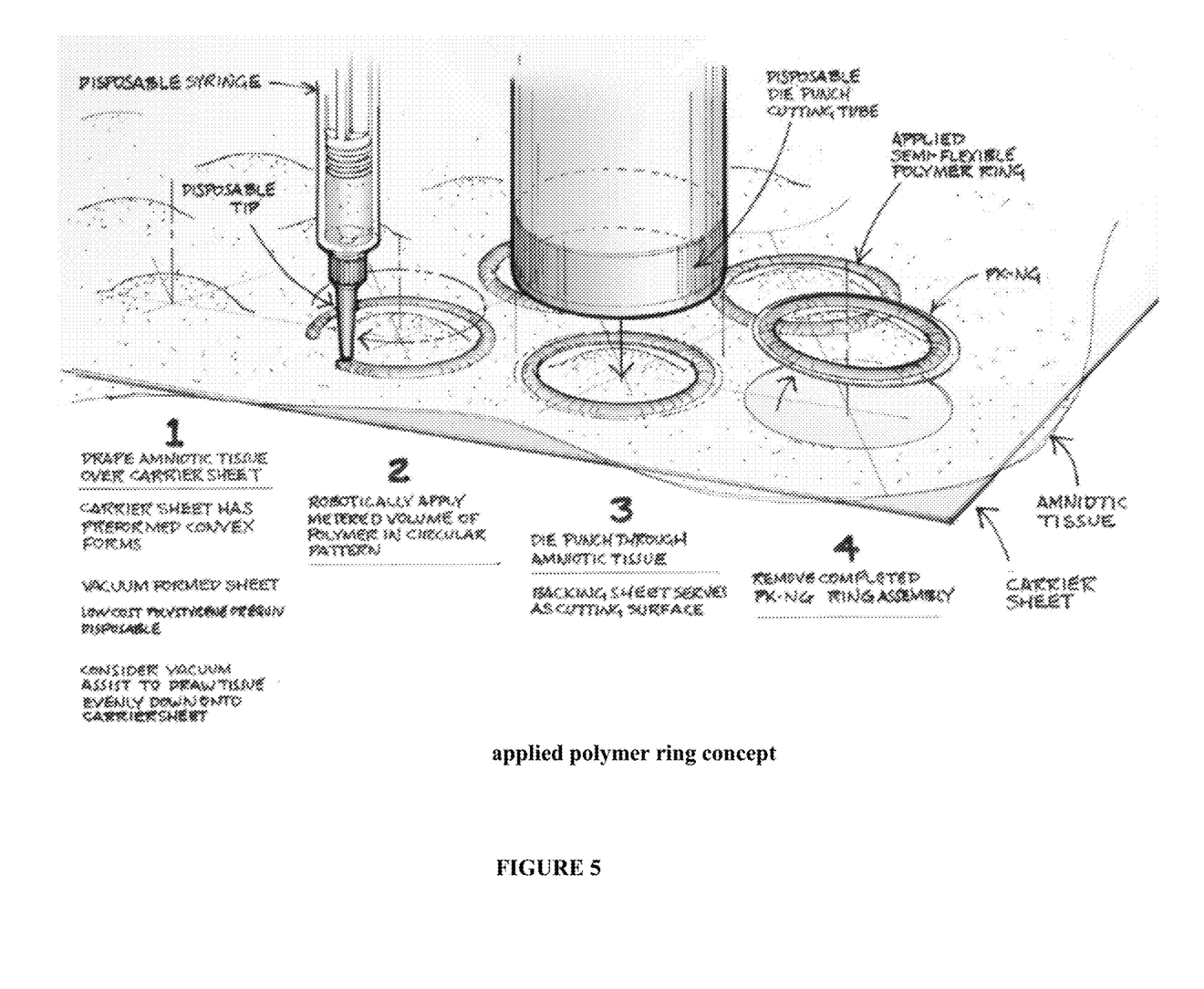
FIG. 5—Illustrates and apparatus of the present application, wherein the apparatuus comprises: at least one sheet of a therapeutic agent and at least one tubular structure of a polymeric material, wherein the tubular structure is formed upon and adhered to the sheet of the therapeutic agent.

In a third embodiment the current application describes an apparatus for treating dry eye or other diseases or disorders of the eye, by insertion of the device onto the surface of the eye of a patient in need thereof, wherein the apparatus comprises: at least one sheet comprising a material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof; and at least one tubular structure comprising a second material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof, wherein at least one sheet and at least one tubular structure are adhering to maintain physical contact with one another.

In some embodiments the apparatus is configured to reside in at least one of the group consisting of: superior conjunctiva fornix, inferior conjunctiva fornix and combinations thereof. In other embodiments the apparatus is configured to reside in both conjunctiva fornices. In certain embodiments the apparatus induces blinking. In still other embodiments the apparatus deepens the fornix tear reservoir by stretching the conjunctival sac.

In some embodiments the at least one tubular structure has a circumference of about 2 cm to about 15 cm, the at least one tubular structure has a circumference of about 4 cm to about 12 cm, the at least one tubular structure has an outside diameter of about 0.5 cm to about 5.0 cm or the at least one tubular structure has an outside diameter of about 1.2 cm to about 3.5 cm, the at least one tubular structure has a cross sectional diameter of about 0.01 cm to about 1.0 cm or the at least one tubular structure has a cross sectional diameter of about 0.05 cm to about 0.2 cm In other embodiments the apparatus is configured to deliver one or more additional therapeutic agents to the patient, the one or more additional therapeutic agents may be incorporated into the material of the at least one tubular structure, on the surface of the at least one tubular structure or combinations thereof, the at least one tubular structure is configured to dissolve when in contact with tears in the patient's eye, the one or more additional therapeutic agents is selected from the group consisting of: antibacterial antibiotics, synthetic antibacterials, antifungal antibiotics, synthetic antifungals, umbilical cord tissue, amniotic membrane tissue, placental tissue, chorion tissue, antineoplastic agents, steroidal anti-inflammatory agents, non-steroidal anti-inflammatory agents, anti-allergic agents, glaucoma-treating agents, antiviral agents, and anti-mycotic agents, the umbilical cord tissue, amniotic membrane tissue, placental tissue or chorion tissue may be present in any form from the group consisting of: lyophilized, fresh, sheet, morselized, powder matrix, extract, purified extract, previously frozen, suspension and on a physiologically acceptable support, the apparatus further comprises a power source at least one positive electrode and at least one negative electrode wherein the apparatus is configured to introduce an electrical stimulus between about 0.1 milliamps and about 50 milliamps to the muscles of the patient's eyelids.

In certain embodiments the at least one tubular structure is formed upon a surface of the at least one sheet by use of a three-dimensional (3D) printer or the at least one tubular structure is formed upon a surface of the at least one sheet by use of polymer extrusion means.

In a fourth embodiment the current application describes an apparatus for treating dry eye or other diseases or disorders of the eye, by insertion of the device onto the surface of the eye of a patient in need thereof, wherein the apparatus comprises: at least one first sheet comprising a material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof; and at least one second sheet comprising a second material selected from the group consisting of: umbilical cord tissue; amniotic membrane tissue; placental tissue; chorion tissue; ethylene vinyl acetate (EVA); polydimethylsiloxane (PDMS); polymethylmetacrylate (PMMA); polyethylene teraphthalate (PET); fibrins; polycarbonate (PC); hydrogels; polyvinyl chloride (PVC); rubber; latex; polyethylene (PE); silicone; polytetrafluoroethylene (PTFE); polyurethane (PU) and combinations thereof, wherein the at least one first sheet and the at least one second sheet are adhering to maintain physical contact with one another.

In some embodiments the apparatus is configured to reside in at least one of the group consisting of: superior conjunctiva fornix, inferior conjunctiva fornix and combinations thereof. In other embodiments the apparatus is configured to reside in both conjunctiva fornices. In certain embodiments the apparatus induces blinking. In further embodiments the apparatus deepens the fornix tear reservoir by stretching the conjunctival sac.

In some embodiments the apparatus has a circumference of about 2 cm to about 15 cm, the apparatus has a circumference of about 4 cm to about 12 cm, the apparatus has an outside diameter of about 0.5 cm to about 5.0 cm or the apparatus has an outside diameter of about 1.2 cm to about 3.5 cm.

In other embodiments the apparatus is configured to deliver one or more additional therapeutic agents to the patient, the one or more additional therapeutic agents may be incorporated into the material of the polymeric sheet, on the surface of the polymeric sheet or combinations thereof, the polymeric sheet is configured to dissolve when in contact with tears in the patient's eye, the one or more additional therapeutic agents is selected from the group consisting of: antibacterial antibiotics, synthetic antibacterials, antifungal antibiotics, synthetic antifungals, umbilical cord tissue, amniotic membrane tissue, placental tissue, chorion tissue, antineoplastic agents, steroidal anti-inflammatory agents, non-steroidal anti-inflammatory agents, anti-allergic agents, glaucoma-treating agents, antiviral agents, and anti-mycotic agents, the umbilical cord tissue, amniotic membrane tissue, placental tissue or chorion tissue may be present in any form from the group consisting of: lyophilized, fresh, sheet, morselized, powder matrix, extract, purified extract, previously frozen, suspension and on a physiologically acceptable support, the apparatus further comprises a power source at least one positive electrode and at least one negative electrode wherein the apparatus is configured to introduce an electrical stimulus between about 0.1 milliamps and about 50 milliamps to the muscles of the patient's eyelids.

In a fifth embodiment the present application describes the use of an apparatus of the application to promote an increase in tissue sensation, to induce a patient to blink and tear more frequently to prevent dry eye, to promote nerve growth, wherein the increase in nerve growth is between about 10% and about 100%, promote nerve regeneration, wherein the increase in nerve regeneration is between about 10% and about 100%, to reduce an inflammatory response in a contacted tissue, to increase Tear Breakup Time in a patient suffering from dry eye disease, to increase tear osmolarity in a patient suffering from dry eye disease, to decrease corneal straining in a patient suffering from dry eye disease, to increase the score on Schirmer's test in a patient suffering from dry eye disease or combinations thereof.

Ophthalmic Formulations

Unless the intended purpose of use is affected adversely, the apparatuses of the present application may further comprise one or more additional therapeutically-active agents. Specific therapeutically-active agents include, but are not limited to: antibacterial antibiotics, synthetic antibacterials, antifungal antibiotics, synthetic antifungals, antineoplastic agents, steroidal anti-inflammatory agents, non-steroidal anti-inflammatory agents, tissue preparations, anti-allergic agents, glaucoma-treating agents, antiviral agents, and antimycotic agents. Further contemplated are any derivatives of the therapeutically-active agents which may include, but not be limited to: analogs, salts, esters, amines, amides, alcohols and acids derived from an agent of the invention and may be used in place of an agent itself Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), .beta.-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $N_2$-formylsulfisomidine, $N_4$-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, $N_4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of the antineoplastic agents include, but are not limited to: antineoplastc antibiotics and analogs (e.g., aclacinomycins, actinomycin anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites exemplified by folic acid analogs (e.g., denopterin, edatrexate, methotrexate, piritrexim, pteropterin, TOMUDEX®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the non-steroidal anti-inflammatory agents include, but are not limited to: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (erg., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicyl sulfuric acid, salsalate, sulfasalazine), thiazinecarboxamides (e.g., am piroxicam, droxicam, isoxicam, lornoxicam, piroxicam, tenoxicam), E-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of tissue preparations include, but are not limited to: umbilical cord tissue, amniotic membrane tissue, placental tissue and chorion tissue wherein, the umbilical cord tissue, amniotic membrane tissue, placental tissue or chorion tissue may be present in any form from the group consisting of: lyophilized, fresh, sheet, morselized, powder matrix, extract, purified extract, previously frozen, suspension and on a physiologically acceptable support.

Examples of anti-allergic agents include, but are not limited to: tranilast, ketotifen fumarate, pheniramine, diphenhydramine hydrochloride, and sodium cromoglicate.

Examples of glaucoma-treating agents include, but are not limited to: pilocarpine hydrochloride, latanoprost, timolol, and isopropylunoprostone.

Examples of antiviral agents include, but are not limited to: idoxuridine, acyclovir, and trifluorouridine.

Examples of anti-mycotic agents include, but are not limited to: pimaricin, fluconazole, miconazole, amphotericin B, flucytosine, and itraconazole.

Ophthalmic Combinations

Unless the intended purpose of use is affected adversely, the apparatus of the present application may be administered concurrently with one or more therapeutically-active agents. Specific therapeutically-active agents include, but are not limited to: antibacterial antibiotics, synthetic antibacterials, antifungal antibiotics, synthetic antifungals, antineoplastic agents, steroidal anti-inflammatory agents, non-steroidal anti-inflammatory agents, tissue preparations, anti-allergic agents, glaucoma-treating agents, antiviral agents, and anti-mycotic agents. Further contemplated are any derivatives of the therapeutically-active agents which may include, but not be limited to: analogs, salts, esters, amines, amides, alcohols and acids derived from an agent of the invention and may be used in place of an agent itself.

Excipients

The ophthalmic formulations may contain various excipients incorporated ordinarily, such as buffering agents (e.g., phosphate buffers, borate buffers, citrate buffers, tartarate buffers, acetate buffers, amino acids, sodium acetate, sodium citrate and the like), isotonicity agents (e.g., saccharides such as sorbitol, glucose and mannitol, polyhydric alcohols such as glycerin, concentrated glycerin, polyethylene glycol and propylene glycol, salts such as sodium chloride), preservatives or antiseptics (e.g., benzalkonium chloride, benzethonium chloride, p-oxybenzoates such as methyl p-oxybenzoate or ethyl p-oxybenzoate, benzyl alcohol, phenethyl alcohol, sorbic acid or its salt, thimerosal, chlorobutanol, other quaternary amines and the like), solubilizing aids or stabilizing agents (e.g., cyclodextrins and their derivatives, water-soluble polymers such as polyvinyl pyrrolidone, or carbomer, surfactants such as polysorbate 80 (Tween 80)), pH modifiers (e.g., hydrochloric acid, acetic acid, phosphoric acid, sodium hydroxide, potassium hydroxide, ammonium hydroxide and the like), thickening agents (e.g., hydroxyethyl cellulose, hydroxypropyl cellulose, methyl cellulose, hydroxypropylmethyl cellulose, carboxymethyl cellulose and their salts), chelating agents (e.g., sodium edetate, sodium citrate, condensed sodium phosphate) and the like. Descriptions of compounds used in standard ophthalmic formulations may be found in, for example, Remington's Pharmaceutical Sciences, latest edition, Mack Publishing Co. Easton Pa.

Non-limiting examples of the contemplated excipients include a buffer, osmotic agent, demulcent, surfactant, emollient, tonicity agent, and/or a preservative component.

EXAMPLES

Example 1

A circular flexible tubular structure having an inside diameter of 3.5 cm and an annular groove situated at its perimeter was placed on a surface with the annular groove facing upwards. A sheet of amniotic membrane tissue was placed over the circular flexible tubular structure and the sheet was forced into the annular groove such that the sheet and the flexible tubular structure became frictionally engaged with the sheet covering the opening defined by the inside diameter of the flexible tubular structure.

Example 2

A circular flexible tubular structure having an inside diameter of 3.5 cm was placed on a surface. A sheet of amniotic membrane tissue was placed over the circular flexible tubular structure. Two fastening cuffs were placed over different segment of the flexible tubular structure thereby frictionally engaging the sheet between the fastening cuffs and the flexible tubular structure with the sheet covering the opening defined by the inside diameter of the flexible tubular structure.

Although the present disclosure has been described in considerable detail with reference to certain preferred versions thereof, other versions are possible. Therefore, the spirit and scope of the application should not be limited to the description of the preferred versions described herein.

Although compositions, materials, and methods similar or equivalent to those described herein can be used in the practice or testing of the present invention, suitable preparations, methods and materials are described herein. All publications mentioned herein are incorporated by reference in their entirety. In the case of conflict, the present specification, including definitions will control. In addition, the particular embodiments discussed below are illustrative only and not intended to be limiting.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the application, in addition to those described herein, will be apparent to those skilled in the art from the foregoing description. Such modifications are also intended to fall within the scope of the appended claims.

What is claimed is:

1. An apparatus for treating a disease or disorder of an eye of an individual in need thereof, the apparatus comprising:
   (a) an annular tubular structure comprising at least one porous outlet; and wherein the apparatus is configured to reside in a superior conjunctiva fornix, an inferior fornix, or a combination thereof, and to deepen the fornix tear reservoir by stretching the conjunctival sac; and
   (b) a therapeutic agent encapsulated by the tubular structure, the therapeutic agent comprising umbilical cord tissue, amniotic membrane tissue, placental tissue, chorion tissue, or a combination thereof.

2. The apparatus of claim 1, wherein the therapeutic agent comprises amniotic membrane tissue, umbilical cord tissue, or a combination thereof.

3. The apparatus of claim 2, wherein the therapeutic agent comprises morselized amniotic membrane, or morselized umbilical cord.

4. The apparatus of claim 1, wherein the annular tubular structure is a tubular structure comprising ethylene vinyl acetate (EVA), polydimethylsiloxane (PDMS), polymethylmetacrylate (PMMA), polyethylene teraphthalate (PET), fibrins, polycarbonate (PC), hydrogels, polyvinyl chloride (PVC), rubber, latex, polyethylene (PE), silicone, polytetrafluoroethylene (PTFE), polyurethane (PU), or a combination thereof.

5. The apparatus of claim 1, wherein the annular tubular structure has an outside diameter of about 0.5 (centimeters) cm to about 5.0 cm.

6. The apparatus of claim 1, wherein the annular tubular structure has a cross-sectional diameter of about 0.01 cm to 1 cm.

7. The apparatus of claim 1, wherein the annular tubular structure has a cross-sectional diameter of about 0.05 cm to 1 cm and an outside diameter of about 2.6 cm to 2.8 cm.

8. The apparatus of claim 1, wherein the annular tubular structure has a cross-sectional diameter of about 0.1 cm and an outside diameter of about 2.7 cm.

9. The apparatus of claim 1, wherein the annular tubular structure has at least one porous inlet.

10. The apparatus of claim 1, wherein the therapeutic agent further comprises an excipient.

11. The apparatus of claim 10, wherein the excipient comprises a stabilizing agent, a surfactant, a chelating agent, or a combination thereof.

12. A method for treating a disease or disorder of an eye of an individual in need thereof, comprising inserting the apparatus of claim 1 onto the surface of an eye of the individual.

13. The apparatus of claim 1, wherein the annular tubular structure comprises at least one porous inlet and at least one porous outlet.

14. The apparatus of claim 13, wherein the at least one porous inlet and the at least one porous outlet form an osmotic pump when in contact with tears in the individual's eye.

15. The apparatus of claim 1, wherein the annular tubular structure is configured to dissolve when in contact with the tears in the individual's eye.

16. The apparatus of claim 1, wherein the therapeutic agent is present in a form selected from the group consisting of lyophilized, fresh, sheet, morselized, powder matrix, extract, purified extract, previously frozen, and a suspension.

* * * * *